(12) United States Patent
Belotserkovsky

(10) Patent No.: US 11,207,012 B2
(45) Date of Patent: Dec. 28, 2021

(54) METHOD OF DIAGNOSING UROLOGICAL DISORDERS

(71) Applicant: Edward Belotserkovsky, San Francisco, CA (US)

(72) Inventor: Edward Belotserkovsky, San Francisco, CA (US)

( * ) Notice: Subject to any disclaimer, the term of this patent is extended or adjusted under 35 U.S.C. 154(b) by 426 days.

(21) Appl. No.: 16/370,971

(22) Filed: Mar. 30, 2019

(65) Prior Publication Data

US 2019/0223774 A1 Jul. 25, 2019

Related U.S. Application Data

(62) Division of application No. 14/923,411, filed on Oct. 26, 2015, now abandoned.

(51) Int. Cl.
*A61B 5/20* (2006.01)

(52) U.S. Cl.
CPC .............. *A61B 5/202* (2013.01); *A61B 5/208* (2013.01)

(58) Field of Classification Search
None
See application file for complete search history.

(56) References Cited

U.S. PATENT DOCUMENTS

| | | | | |
|---|---|---|---|---|
| 3,363,619 A * | 1/1968 | Keitzer | ................... | A61B 7/008 600/584 |
| 5,078,012 A * | 1/1992 | Ding | ...................... | A61B 5/208 600/573 |
| 5,377,101 A * | 12/1994 | Rollema | ................. | A61B 5/208 600/584 |
| 2004/0015100 A1* | 1/2004 | Schmidt | ................. | A61B 5/205 600/561 |
| 2008/0082022 A1* | 4/2008 | Brohan | .................. | A61B 5/208 600/573 |
| 2008/0275366 A1* | 11/2008 | Brohan | .................. | A61B 5/208 600/584 |
| 2012/0048033 A1* | 3/2012 | Belotserkovsky | ...... | G01F 1/666 73/861.18 |
| 2012/0053540 A1* | 3/2012 | Belotserkovsky | ....... | A61B 7/00 604/317 |
| 2016/0183803 A1* | 6/2016 | Mosli | ................... | A61B 5/1128 600/476 |

* cited by examiner

*Primary Examiner* — Matthew Kremer
(74) *Attorney, Agent, or Firm* — Charles H. Jew

(57) ABSTRACT

Parametrical analysis of uroflowmetry test results identifies urological disorders so as to distinguish men who have a low urinary tract disorder/benign prostatic hyperplasia from those who have an overactive bladder. Primary urine flow dynamic parameters and secondary urine flow dynamic parameters are calculated. Patient's urological disorders can be assessed by comparing the primary and secondary urine flow dynamic parameters with a library or database of comparable data derived from healthy or normal individuals as well as comparable data derived from individuals afflicted with specific urological disorders. A predictive model of lower urinary tract function disorders can be developed from existing reference primary and secondary urine flow dynamic parameters. The model allows for complex analysis and objective disease prediction.

17 Claims, 4 Drawing Sheets

METHOD OF DIAGNOSING UROLOGICAL DISORDERS

REFERENCE TO RELATED APPLICATIONS

This application is a divisional application of U.S. patent application Ser. No. 14/923,411, that was filed on Oct. 26, 2015, which claimed priority to U.S. provisional application 62/068,763 that was filed on Oct. 27, 2014.

FIELD OF THE INVENTION

The present invention generally relates to techniques for diagnosing urological disorders by analyzing a patient's uroflowmetry test data.

BACKGROUND OF THE INVENTION

Low urinary tract disorder symptoms/benign prostatic hyperplasia (LUTS/BPH) and overactive bladder (OAB) are two very common urinary disorders which result in practically the same symptoms but require different medical treatments. LUTS/BPH refers to symptoms caused by obstruction which can include various degrees of poor urine flow, hesitancy and intermittency. OAB is a syndrome or symptom complex defined as: Urgency, with or without urgency incontinence, usually with frequency and nocturia. Urgency is defined as a sudden, compelling need to avid which is difficult to defer. Frequency is defined as voiding more than 8 times a day. Nocturia is defined a voiding more than one per night. The first disorder is considered obstructive whereas the second one is considered non-obstructive.

In males, the urethra travels through the prostate gland. With aging, the prostate gland enlarges, and muscle cells within prostate and bladder neck tighten. The combination of enlargement and muscle tightening causes compression of the urethra and obstruction of urine flow. One type of nerve that controls muscle cell tightening is the alpha adrenergic nerves which release a chemical related to epinephrine. FLOMAX (tamsulosine) blocks the effects of this chemical on the muscle cells, causing muscles to relax. This decreases obstruction to flow of urine.

OAB affects both young and old adults and its prevalence increases with age. OAB symptoms are treated with anticholinergic medicines which block nerves that control bladder muscle contractions and allow for relaxation of bladder muscles.

Diagnosis of urological disorders is often facilitated by a patient's urine flow rate data. Urological disorders such as obstructions in the lower urological tract or neurotic bladder can be detected by studying the patient's urine flow rate as it varies from the beginning of voiding to the end, and the total volume of urine voided. This data can be compared to the mean data for an individual of the same sex and age to help determine the degree of urethral stricture.

Uroflowmetry measures urine voided per unit time, which is usually expressed as milliliters per second. The International Continence Society has standardized certain objective measurements that are recorded during uroflow measurements. These include flow pattern, voided volume, maximum flow rate (Qmax), voiding time, and time to maximum flow as illustrated in FIG. 1.

Flow pattern, Qmax, and volume voided are generally regarded to be the most clinically useful for both screening and monitoring patients. The Qmax is helpful in distinguishing those who have bladder-outlet obstruction (BOO) from those who do not. The following cutoff values for Qmax are widely accepted: rates greater than 20 mL/s indicate a low probability of BOO; rates between 15 mL/s and 20 mL/s indicate a low probability of BOO (but symptomatic patients should be considered for urodynamic studies); rates between 10 mL/s and 15 mL/s are equivocal; and rates less than 10 mL/s are often the result of BOO or detrusor impairment.

While men with LUTS/BPH symptoms can be effectively treated with medical therapies aimed at benign prostatic enlargement, the degree of improvement is often modest. Moreover, a subset of men show minimal improvement. One explanation for this is the physician's inability to differentiate between symptoms attributable to detrusor over activity/overactive bladder (DO/OAB) to those caused by bladder-outlet obstruction that is secondary to benign prostatic enlargement. Studies have highlighted the difficulties with linking specific LUTS with urodynamic findings, which implies that the choice of medical therapy (i.e. whether it is directed at the bladder or the prostate) is often empirical.

A role for antimuscarinic agents has been suggested for men with LUTS/BPH, although the selection of men who will benefit most from monotherapy versus combined therapy and the clarification of long-term safety concerns, remain important and somewhat contentious issues. Urodynamic information might be helpful in determining which patients would benefit most from alpha blocker monotherapy or combination therapy, respectively. There is need for effective methods of diagnosing urological disorders such as differentiating between LUTS and OAB and particularly between LUTS/BPH and OAB in men.

SUMMARY OF THE INVENTION

The present invention is based in part on the recognition that parametrical analysis of uroflowmetry test results can be employed to identify the type of urological disorder(s) that a patient might be afflicted with. The present invention can be employed to assess urological disorders in general, and in one particular application, the parametrical analysis can distinguish men who have low urinary tract disorder/benign prostatic hyperplasia from those who have overactive bladders.

Uroflowmetry test results are data of a male or female patient's urination flow. Once this information is available, primary urine flow dynamic parameters, which are generally defined as the patient's measured urination flow time and volume characteristics are calculated. Preferred primary urine flow dynamic parameters include, for example, (1) maximum urine flow rate (Qmax), (2) average urine flow rate (Qave), (3) time to maximum urine flow rate, (4) total voided urine volume, (5) void time (or actual void time) and (6) total time (which is the time period from when the patient initiates urination to when urination stops). Total time is usually longer than the void time which is the period from actual urination to cessation of urination. Thereafter, secondary urine flow dynamic parameters, which are generally defined as selective urination parameters derived from the primary parameters are calculated. Preferred secondary urine flow dynamic parameters include, for example, (1) flow acceleration, (2) number of peaks (or number of valleys) in the urination pattern, (3) average flow to maximum flow ratio (Qave/Qmax), (4) time-to-maximum flow to total void time ratio, (5) void time to total time ratio, (6) "plateau" time, (7) "plateau" time to total void time ratio, and (8) "plateau time" to total time ratio.

The flow acceleration is defined as the (dF/dt) or slope at the beginning of the patient's urination. This parameter indicates how quickly the urination flow rate reaches maximum. The ratio of Qmax to time-to-maximum urine flow rate is a close approximation of the flow acceleration. The number of peaks (or number of valleys) can be calculated based on the flow first differential (dF/dt) which changes in sign from + to − at the peak and from − to + at the valley. The "plateau" time is the time period when the urination flow rate is 0.9 Qmax or higher.

It is expected that individuals suffering from urological disorders that are either obstructive or non-obstructive in nature will exhibit characteristic or signature primary and secondary urine flow dynamic parameters when their uroflowmetry test results are analyzed. That is, at least some of these parameters will be statistically significant and correlate to specific urological disorders. Thus, a patient's urological disorder(s) can be identified and assessed by comparing his or her primary and secondary urine flow dynamic parameters to a library or database of comparable data derived from healthy or normal individuals as well as comparable data derived from individuals afflicted with specific urological disorders.

The inventive technique further includes a combined analysis of the patient's condition based on the both primary and secondary urine flow dynamic parameters. The analysis can include the patient's medical history including, for example, gender, age, height, weight, blood pressure and ethnicity. Once evaluation is made, proper treatment can be administered by the physician.

In a preferred embodiment, a predictive model of lower urinary tract function disorders can be developed from existing reference primary and secondary urine flow dynamic parameters. The model, which is typically expressed as a formula, allows for complex analysis and objective disease prediction. Thus a patient's urological disorder, if any, can be predicted by applying the model to the patient's primary and secondary urine flow dynamic parameters.

DETAIL DESCRIPTION OF PREFERRED EMBODIMENTS

Figure 1:
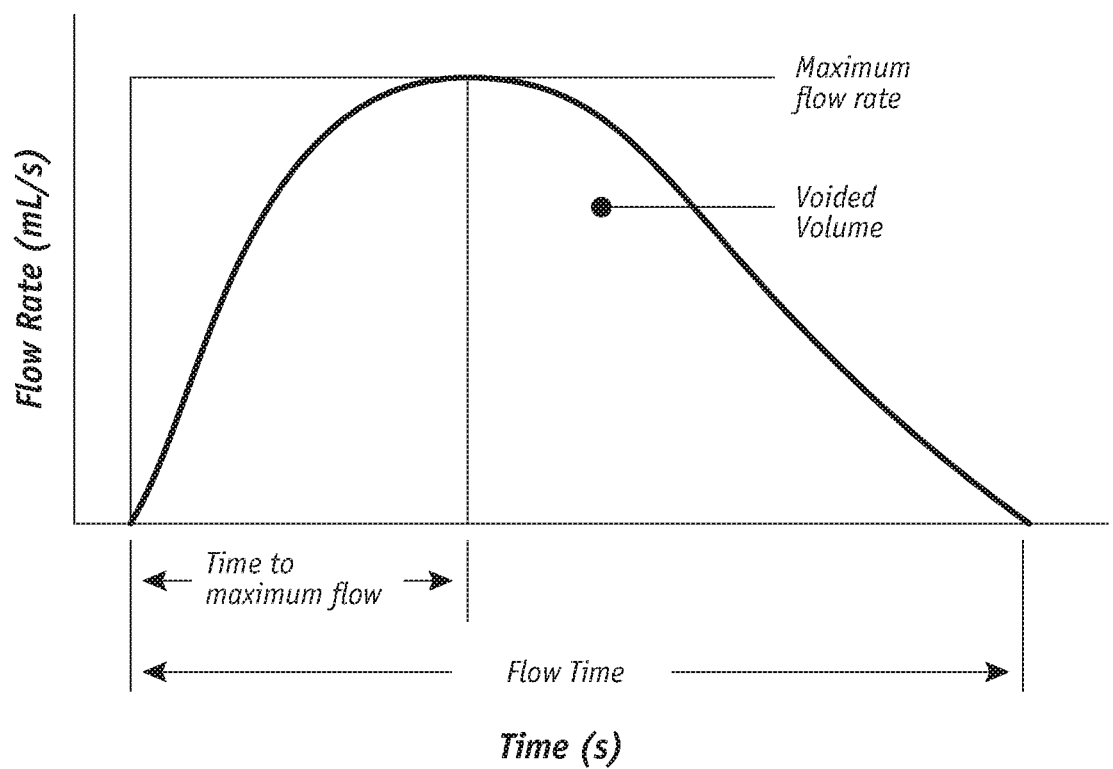
FIG. 1 is a graph illustrating various conventional uroflow measurements.

As shown in FIG. 1, a patient's urination pattern is monitored using a urine flow monitor 1 which can be any suitable urine flow meter that yields urine flow data. Commercially available monitors include, for example, mechanical urine flow meter devices that include a container having a graduated scale for indicating the volume of urine within the container. Urine flow is detected by observing the change in volume as the patient voids into the container. Electrical urine flow meters for providing urine flow data have a urine velocity-measuring apparatus in the form of a urine flow receptacle with a paddle wheel journaled therein. The paddle wheel is mechanically linked to a generator, which produces an output voltage that is displayed on a voltmeter. The velocity of the urine stream impinging on the paddle wheel determines the paddle wheel velocity and therefore the output voltage of the generator. Other urine flow devices include a urine-receiving receptacle that has a pair of parallel spaced-apart rods or strips disposed therein. The rods or strips are electrically connected to a capacitance sensing circuit. As the volume of urine within the receptacle increases, the capacitance between the rods also increases so that by measuring the rate of change of the capacitance, an indication of the urine flow may be obtained.

A particularly suitable urine flow monitoring device is disclosed in U.S. Pat. No. 8,567,258 to Belotserkovsky which is incorporated herein by reference. During urination (or voiding process) the unique characteristic sounds that are produced by the urine as it impacts the surface of the water in a toilet or urinal can be used to monitor the person's urinary flow pattern and its dynamics. Because the sound's intensity (loudness) and spectrum depend on the urine flow level, by detecting the intensity at selected acoustic frequencies, it is possible to accurately and precisely measure the urine flow rate.

The Belotserkovsky device can be employed to analyze urine flow and its dynamics by using sound levels that are detected at two or more distinct frequency regions or channels of the sound spectrum. One frequency region that is designated the measurement channel is where the sound measurement intensity or output strongly depends on urine flow levels. Another frequency region that is designated the reference channel is where the sound measurement intensity is not dependent on urine flow levels. By using a combination of measurements from the measurement channel and the reference channel, the urine flow monitoring apparatus compensates for variations in operating conditions and other factors during use.

Figure 3:
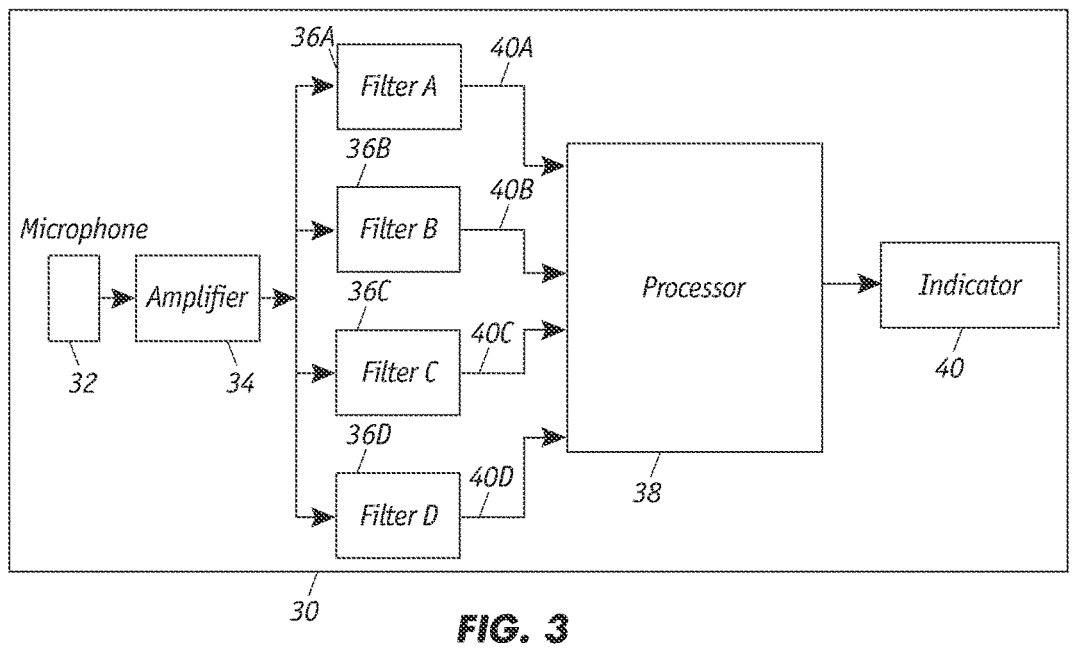
FIG. 3 is an acoustic urine flow monitoring device.

In one embodiment of the Belotserkovsky device as illustrated in FIG. 3 includes a microphone for detecting acoustical sound that is generated as urine impacts a liquid surface. The medical urine flow monitoring device 30 includes a microphone 32, amplifier 34, a bank of filters that includes filters 36A, 36B, 36C and 36D, a signal processor 38 and an output indicator 40. Electrical signals from microphone 32, which can be omnidirectional or unidirectional microphone(s), are amplified by amplifier 34 before being passed through the plurality of filters that produce filtered signals 40A, 40B, 40C, and 40D, respectively. The bank of filters serves to select the filtered signals of the desired frequency ranges to be analyzed by processor 38. FIG. 3 depicts a four-channel urine flow-monitoring device with each channel employing a different type of filter. Preferably one or more of the channels measure sound level with frequencies in a measurement range and one or more of the channels measure sound level with frequencies in a reference range.

Figure 2:
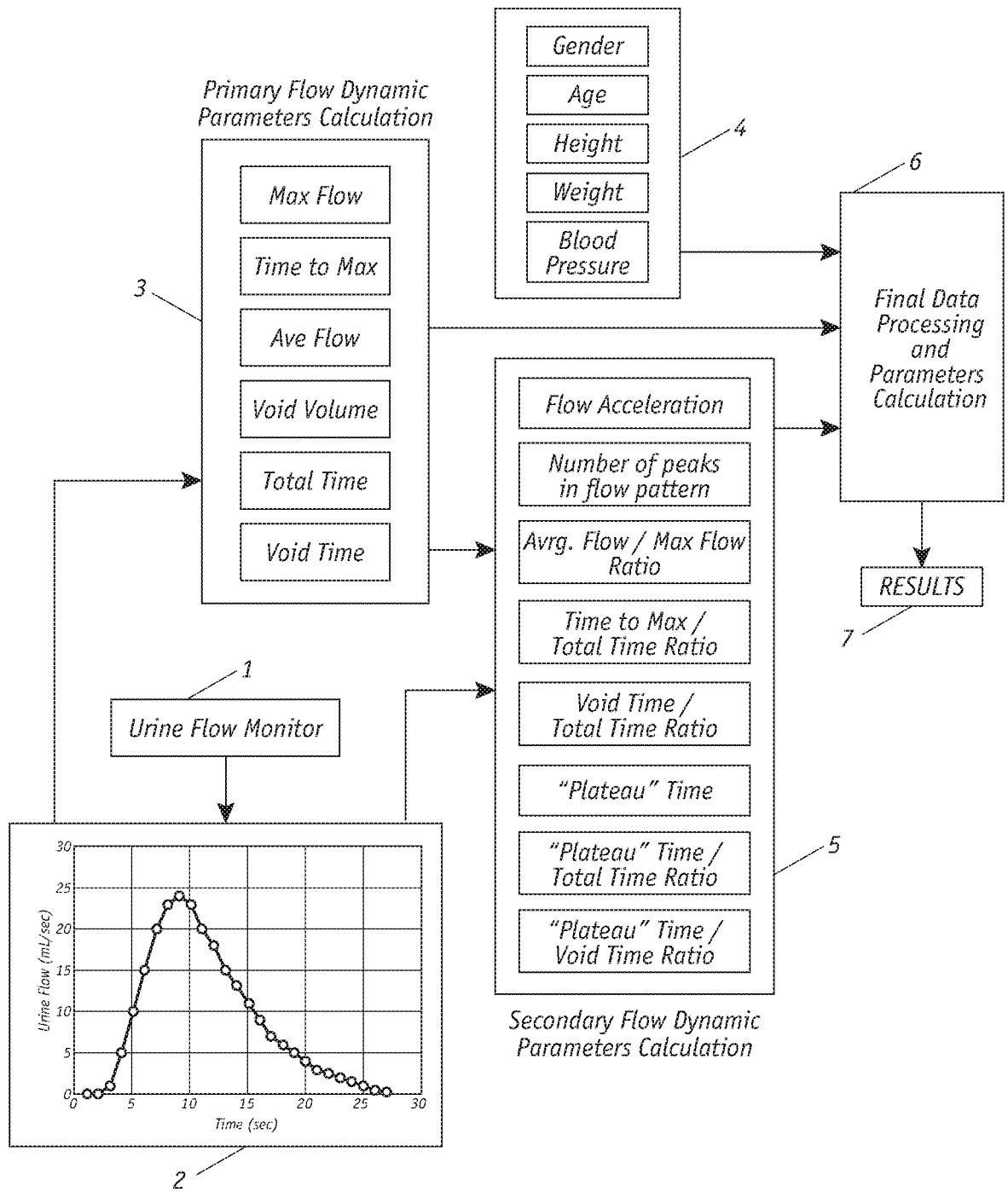
FIG. 2 depicts a procedure for assessing urological disorders.

Referring to FIG. 2, once a patient's urination pattern is detected and recorded, the urine flow monitoring device 1 generates a graph 2 of the patient's urine flow pattern which is flow rate vs. time as depicted. The primary flow dynamic parameters 3 and secondary flow dynamic parameters 5 are calculated.

Typically at least two and preferably at least five primary flow dynamic parameters are calculated and employed. Similarly, at least two and preferably at least five secondary flow dynamic parameters are calculated and employed; in this regard, the flow acceleration, can be derived from the urine flow pattern 2 as being the flow slope–$1^{st}$ differential of function Q=F(t):dF(t)/dt). Graph 2 only shows a single peak in the urine flow pattern.

Both primary and secondary dynamic parameters calculations along with patient medical history including, for sample, gender, age, weight, height and blood pressure are taken into consideration during final data processing and parameters calculation in step 6. Diagnostic results 7 indicate the likelihood of whether the patient has a urological disorder and if so the probability of whether the condition is LUTS, OAB or other urological condition.

The present invention can also be implemented as a standalone application which uses saved data files or printouts of previously conducted tests by digitizing their images. The files can be in .TXT, .DAT, .XLS, .CSV or of other format, which can be downloaded or imported from an external or internal database. Alternatively, the files can be generated by taking an image of a urine flow graph derived from an uroflowmetry test. This can be achieved by taking a picture of the graph printout and digitizing it using a camera in a smartphone, tablet or other device. A developed application of the standalone program can be installed into Windows or Apple based PCs or laptops as well as into tablets, smartphones or other processing devices.

Figure 4:
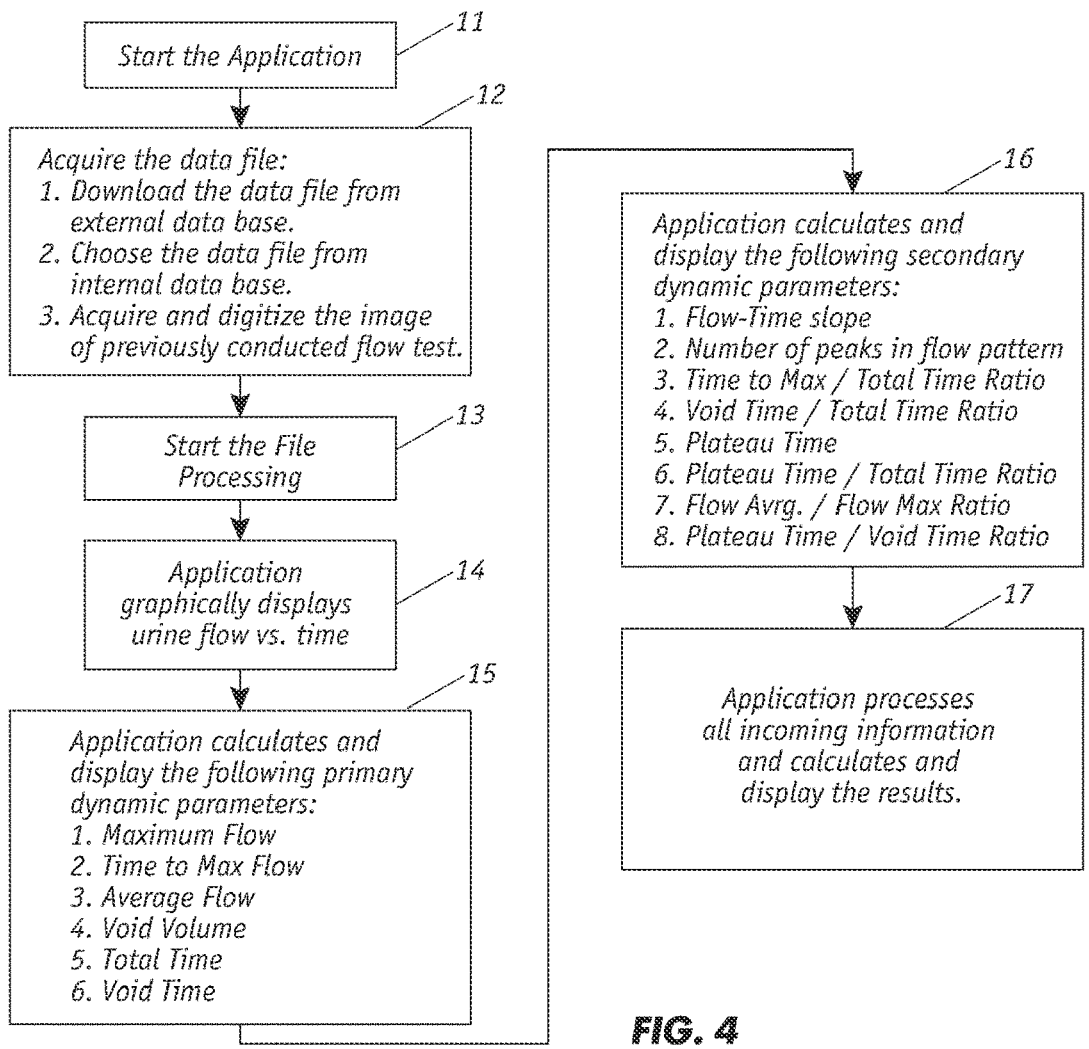
FIG. 4 illustrates an application for executing the diagnostic technique.
Figure 5:
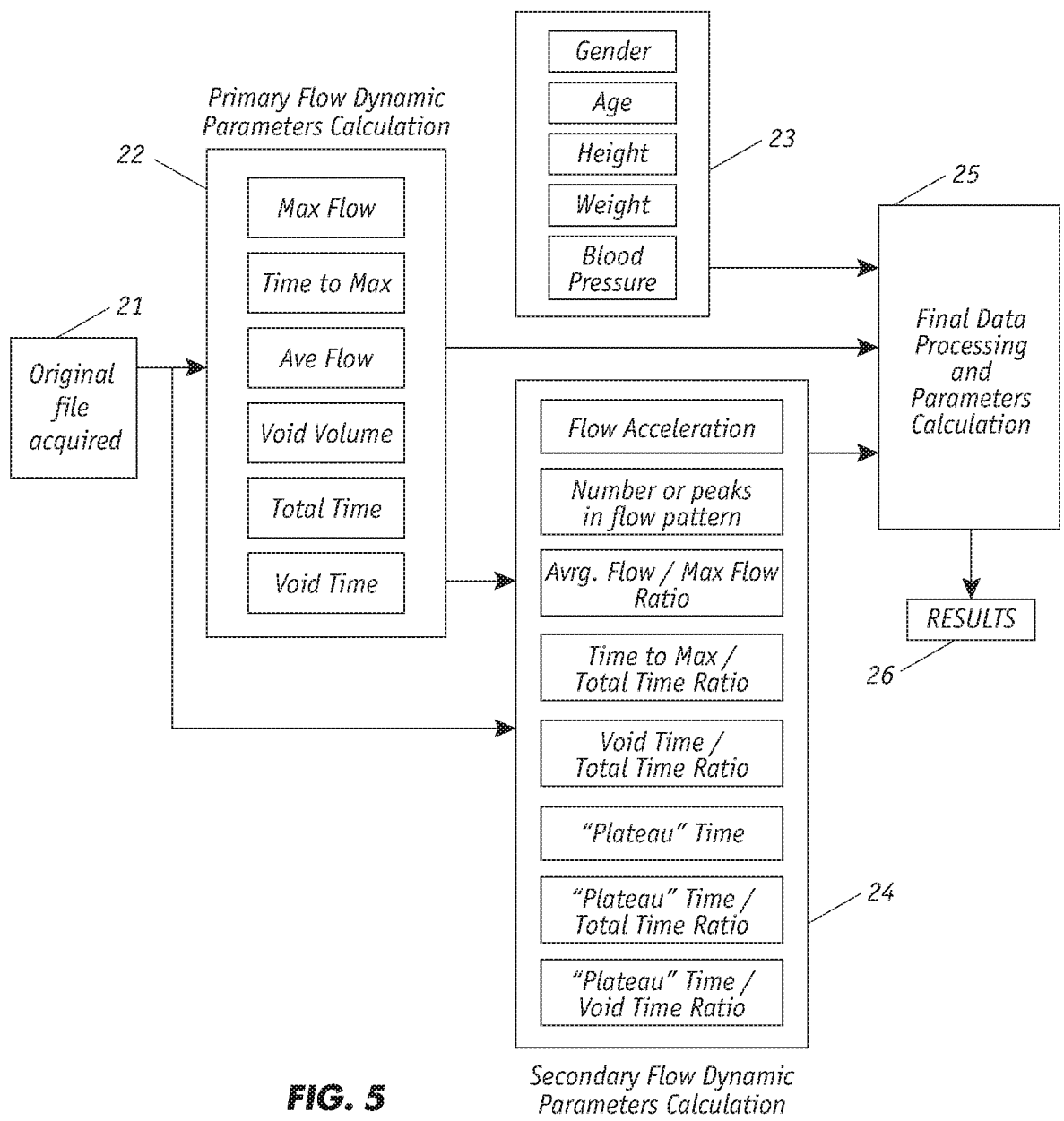
FIG. 5 illustrates data processing and parameters calculation.

As shown in FIG. 4, in step 11 the user starts the application and acquires the uroflowmetry data file in step 12. Thereafter, the application is initiated in step 13 and the application displays the urine flow pattern in step 14. The primary dynamic parameters are calculated and displayed in step 15, the secondary dynamic parameters are determined in step 16 and the results displayed in step 17.

It is expected that healthy individuals and particularly those who do not have urological disorders will exhibit characteristic primary and second dynamic parameters. A reference database of such normal parameters obtained from clinical uroflowmetry tests from healthy individual can be generated; moreover, the reference database can be further sub-classified according to health history including, for example, gender, age, height, weight, blood pressure and ethnicity of the individuals. Similarly, it is expected that individuals who are classified has suffering from urological disorders will exhibit characteristic primary and second dynamic parameters. A reference database of such abnormal parameters obtained from clinical uroflowmetry tests from individual having particular forms of urological disorders can be generated; moreover, the reference database can be further classified according to the health history. Typically, for the normal reference database, each primary and secondary parameter will be assigned a range; similarly, for the abnormal database each primary and secondary parameter will be assigned a range.

With the present invention, a patient in need of urological assessment will undergo an uroflowmetry test and his or her primary and secondary dynamic parameters will be compared to the reference database from healthy and inflicted individual. The results will indicate the degree to which the patient's primary and second dynamic parameters match those of normal and/or abnormal references. It is expected that for any particularly urological disorder, not all of the primary urine flow dynamic parameters are equal and not all of the secondary urine flow dynamic parameters. In other words, some parameters might be more indicative of a particular urological disorder than other parameters. Thus, the various parameters can be weighted in accordance to their degree of relevance to the diagnosis to enhance the comparison step.

In analyzing the primary and secondary urine flow dynamic parameters, instead of comparing the patient's primary and secondary dynamic parameters to the reference database from healthy and inflicted individual, a predictive mathematical model that uses the patient's primary and secondary dynamic parameters, as well as other variables such as medical history information, can be employed. The model can be developed using the reference database. In this embodiment, predictive modeling of the lower urinary tract function disorders analyzes the patient's primary and secondary urine flow dynamic parameters and generates an assessment or prediction of the patient's urological condition.

Once the results are available, the physician determines the proper course of treatment for those suffering from urological disorders. Treatment may consist solely of behavioral changes where the patient has symptoms. Medication may be required. For BPH indications, available drugs include, for example, (1) alpha-blockers (non uroseletive) such as HYTRIN (terazosin) and CARDURA (doxazosin), (2) alpha-blockers (uroselective) such as UROXATRAL (alfuzosin), REPALFO (silodosin) and FLOMAX (tamsulosin), (3) phosphodiesterase 5 inhibitors such as CIALIS (tadalafil), and (4) 5 alpha reductase inhibitors such as AVODART (dutasteride) and PROSCAR (finasteride).

For OAB indications, available drugs include, for example, (1) antimuscarinisc—immediate release (IR) such as DITROPAN (oxybutynin IR), DETROL (tolterodine IR), and SANCTURA (trospium chloride), (2) antimuscarinics—extended release (ER), such as ENABLEX (darifenacin ER), TOVIAZ (fesoterodine ER), DITROPHAN XL (oxybutynin ER), OXYTROL (oxybutynin TDS), GELNIQUE (oxybutynin 10% gel), VSICARE (solifenacin), DETROL LA (tolterodine ER) and SANCTURE XR (tropismum chloride), and (3) beta 3 agonists such as MYRBETRIQ (mirabegron). Surgery may be required in severe cases.

Figure 6:
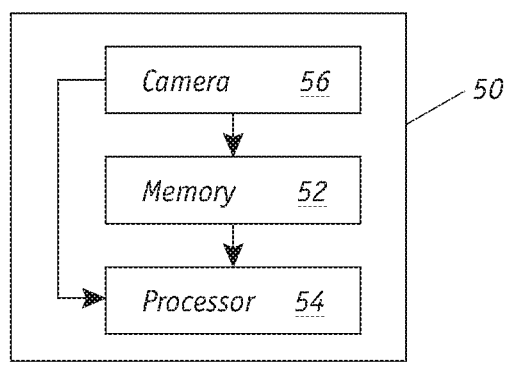
FIG. 6 is a computerized system for assessing urological disorders.

FIG. 6 is a computerized system 50 for assessing urological disorders which includes a memory 52 for storing database patient's uroflowmetry data that includes the individual's voiding flow rate over time. The process 52 calculates the primary and secondary urine flow dynamic parameters and analyzes the primary and secondary urine flow dynamic parameters. In the case where the computerized system 50 is incorporated in a smartphone or tablet, a camera 56 can be employed to take images of urine flow patterns.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A method of determining an individual's urological condition comprising:
   (a) acquiring the individual's uroflowmetry data by (i) detecting acoustic energy that is generated as urine, from the individual during urination, impacts a liquid surface, (ii) converting the acoustic energy into electrical signals, (iii) converting the electrical signals into digital form, (iv) extracting filtered signals from the electrical signals in digital form with a digital filter; and (v) processing the filtered signals to generate output signals that represent the individual's acquired uroflowmetry data;
   (b) calculating primary urine flow dynamic parameters from the uroflowmetry data wherein the calculated primary urine flow dynamic parameters include maximum urine flow, time to maximum urine flow, average urine flow, voided urine volume, void time, which is a time period that the urine impacts the liquid surface, and total void time, which is a time period from when the individual initiates the urination to when urine flow of the urination stops;
(c) calculating secondary urine flow dynamic parameters from the primary urine flow dynamic parameters wherein the calculated secondary urine flow dynamic parameters include urine flow acceleration, average urine flow to maximum urine flow ratio, time-to-maximum urine flow to total void time ratio, and "Plateau" time to void time ratio;
(d) comparing the individual's primary and secondary urine flow dynamic parameters to first reference primary and secondary urine flow dynamic parameters that are obtained from other individuals having urological disorders and/or to second reference primary and secondary urine flow dynamic parameters that are obtained from healthy individuals; and
(e) determining the individual's urological condition based on the comparison made in step (d).

2. The method of claim 1 wherein the first reference primary and secondary urine flow dynamic parameters correlate to the urological disorders.

3. The method of claim 2 further comprising treating the individual to alleviate the individual's urological condition by administering a drug or pharmaceutically acceptable salt thereof.

4. The method of claim 1 wherein the calculated secondary urine flow dynamic parameters further include at least one of void time to total void time ratio or "Plateau" time.

5. The method of claim 1 further comprising differentiating the individual's urological condition as being a low urinary tract disorder or an overactive bladder.

6. A method of determining an individual's urological condition comprising:
(a) acquiring the individual's uroflowmetry data by (i) detecting acoustic energy that is generated as urine, from the individual during urination, impacts a liquid surface, (ii) converting the acoustic energy into electrical signals, (iii) converting the electrical signals into digital form, (iv) extracting filtered signals from the electrical signals in digital form with a digital filter; and (v) processing the filtered signals to generate output signals that represent the individual's acquired uroflowmetry data;
(b) calculating primary urine flow dynamic parameters from the uroflowmetry data wherein the calculated primary urine flow dynamic parameters include maximum urine flow by the individual during the urination, time to maximum urine flow, average urine flow, voided urine volume, void time, which is a time period that the urine impacts the liquid surface, and total void time, which is a time period from when the individual initiates the urination to when urine flow of the urination stops;
(c) calculating secondary urine flow dynamic parameters from the primary urine flow dynamic parameters wherein the calculated secondary urine flow dynamic parameters include urine flow acceleration, average urine flow to maximum urine flow ratio, time-to-maximum urine flow to total void time ratio, and "Plateau" time to void time ratio;
(d) using reference primary and secondary urine flow dynamic parameters from a reference population to develop a model that predicts a person's urological condition based on the person's primary and secondary urine flow dynamic parameters; and
(e) applying the model to the individual's primary and secondary urine flow dynamic parameters to determine the individual's urological condition.

7. The method of claim 6 further comprising treating the individual to alleviate the indivdual's urological condition by administering a drug or pharmaceutically acceptable salt thereof.

8. The method of claim 6 wherein the calculated secondary urine flow dynamic parameters further include at least one of void time to total void time ratio or "Plateau" time.

9. The method of claim 8 wherein the reference population comprises a population comprising other individuals with urological disorders.

10. The method of claim 9 wherein the reference population has a known medical history to that of the individual.

11. The method of claim 10 wherein the medical history includes one or more patient information that is selected from the group consisting of the individual's gender, age, height, weight, blood pressure, ethnicity, and combination thereof.

12. The method of claim 6 further comprising differentiating the individual's urological condition as being a low urinary tract disorder or an overactive bladder.

13. A method of determining an individual's urological disorder comprising:
(a) acquiring the individual's uroflowmetry data by measuring the individual's voiding volume versus voiding time during urination whereby the individual's urine flow rate during the urination is measured by detecting, at different acoustic frequencies, an intensity of sound that is produced by urine as it impacts a liquid surface;
(b) calculating primary urine flow dynamic parameters from the uroflowmetry data wherein the calculated primary urine flow dynamic parameters include maximum urine flow, time to maximum urine flow, average urine flow, voided urine volume, void time, which is a time period that the urine flows from the individual, and total void time, which is a time period from when the individual initiates the urination to when urine flow stops;
(c) calculating secondary urine flow dynamic parameters from the primary urine flow dynamic parameters wherein the calculated secondary urine flow dynamic parameters include urine flow acceleration, average urine flow to maximum urine flow ratio, time-to-maximum urine flow to total void time ratio, and "Plateau" time to void time ratio; and
(d) comparing the individual's primary and secondary urine flow dynamic parameters to reference primary and secondary urine flow dynamic parameters from a reference population to determine the individual's urological disorder.

14. The method of claim 13 wherein step (d) detects signature primary and secondary urine flow dynamic parameters that are indicative of different urological disorders.

15. The method of claim 13 wherein step (d) comprises using the reference primary and secondary urine flow dynamic parameters to develop a model that predicts a person's urological condition based on the person's primary and secondary urine flow dynamic parameters and applying the model to the individual's primary and secondary urine flow dynamic parameters to determine the individual's urological disorder.

16. The method of claim 13 wherein the calculated secondary urine flow dynamic parameters further include at least one of void time to total void time ratio or "Plateau" time.

17. The method of claim 13 wherein step (a) comprises (i) detecting the intensity of sound that is generated as the urine, from the individual during the urination, impacts the liquid surface, (ii) converting the intensity of sound that is detected into electrical signals, (iii) converting the electrical signals into digital form, (iv) extracting filtered signals from the electrical signals in digital form with a digital filter; and (v) processing the filtered signals to generate output signals that represent the individual's acquired uroflowmetry data.

\* \* \* \* \*